United States Patent
Kim et al.

(10) Patent No.: US 10,308,566 B1
(45) Date of Patent: Jun. 4, 2019

(54) METHOD OF SEPARATING NORMAL BUTENE USING ISOMERIZATION AND PROCESS SYSTEM FOR SEPARATING NORMAL BUTENE

(71) Applicant: LG CHEM, LTD., Seoul (KR)

(72) Inventors: Dae Hyeon Kim, Daejeon (KR); Soo Hwan Hwang, Daejeon (KR); Jong Ku Lee, Daejeon (KR); Jeong Seok Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 16/250,811

(22) Filed: Jan. 17, 2019

Related U.S. Application Data (62) Division of application No. 15/325,329, filed as application No. PCT/KR2016/004459 on Apr. 28, 2016, now Pat. No. 10,227,270.

(30) Foreign Application Priority Data

May 13, 2015 (KR) .......................... 10-2015-0066867

(51) Int. Cl.
 *B01D 3/00* (2006.01)
 *C07C 5/25* (2006.01)
 *C07C 7/04* (2006.01)

(52) U.S. Cl.
 CPC ............ *C07C 5/2556* (2013.01); *B01D 3/007* (2013.01); *B01D 3/009* (2013.01); *C07C 7/04* (2013.01); *Y02P 30/48* (2015.11)

(58) Field of Classification Search
 CPC ...... B01D 3/007; B01D 3/009; C07C 5/2556; C07C 7/04; C07C 11/09; C07C 7/005; C07C 11/08; C07C 7/148
 See application file for complete search history.

(56) References Cited

U.S. PATENT DOCUMENTS

| 5,955,640 A | 9/1999 | Paludetto et al. |
| 6,215,036 B1 | 4/2001 | Dorbon et al. |

(Continued)

FOREIGN PATENT DOCUMENTS

| CN | 1144793 | 3/1997 |
| CN | 1226227 | 8/1999 |

(Continued)

OTHER PUBLICATIONS

International Search Report and the Written Opinion of PCT/KR2016/004459, dated Aug. 3, 2016.

(Continued)

*Primary Examiner* — Sharon Pregler
(74) *Attorney, Agent, or Firm* — Dentons US LLP (57) ABSTRACT

Provided are a separation system for easily recovering normal butene from an olefin fraction including isobutene, isobutane, 1-butene, 2-butene, and normal butane, and a separation process system using the method. Since the separation system may easily convert 1-butene included in the olefin fraction to 2-butene, normal butene may be effectively separated and recovered by factional distillation and each recovered fraction may be easily refluxed even if the use of a reflux system using a refrigerant is reduced or excluded. Thus, economic efficiency may be improved and simultaneously, separation efficiency may be increased.

7 Claims, 2 Drawing Sheets

(56) References Cited

U.S. PATENT DOCUMENTS

| | | | |
|---|---|---|---|
| 6,242,661 B1 | 6/2001 | Podrebarac et al. | |
| 7,982,086 B2 * | 7/2011 | Almering | C07C 7/005 585/664 |
| 2006/0235252 A1 | 10/2006 | Gartside et al. | |
| 2006/0235254 A1 | 10/2006 | Gartside et al. | |
| 2006/0235255 A1 | 10/2006 | Gartside et al. | |
| 2010/0197987 A1 | 8/2010 | Almering | |
| 2013/0204057 A1 | 8/2013 | Adam et al. | |
| 2013/0245348 A1 | 9/2013 | Vermeiren et al. | |

FOREIGN PATENT DOCUMENTS

| | | |
|---|---|---|
| CN | 101792363 | 8/2010 |
| CN | 102892729 | 1/2013 |
| EP | 0474188 | 3/1992 |
| EP | 0971517 | 1/2000 |
| JP | 2000-029848 | 1/2000 |
| JP | 2000282273 | 10/2000 |
| JP | 2003505353 | 2/2003 |
| JP | 2008536848 | 9/2008 |
| JP | 2008536849 | 9/2008 |
| JP | 2008536863 | 9/2008 |
| JP | 2012516846 | 7/2012 |
| JP | 2012167852 | 9/2012 |
| KR | 10-1992-0006264 | 4/1992 |
| KR | 10-1997-0001286 | 1/1997 |
| KR | 10-2000-0029848 | 5/2000 |
| KR | 10-2012-0128685 | 11/2012 |

OTHER PUBLICATIONS

Office Action of Japanese Patent Office in Appl'n No. 2016574443 dated Oct. 2, 2018.

Office Action of Chinese Patent Office in Appl'n No. 201680001979.1, dated Sep, 12. 2018.

* cited by examiner

METHOD OF SEPARATING NORMAL BUTENE USING ISOMERIZATION AND PROCESS SYSTEM FOR SEPARATING NORMAL BUTENE

CROSS-REFERENCE TO RELATED APPLICATIONS

This application is a divisional of co-pending, allowed U.S. patent application Ser. No. 15/325,329, which is a National Stage Entry of International Application No. PCT/KR2016/004459, filed on Apr. 28, 2016, and claims the benefit of Korean Patent Application No. 10-2015-0066867, filed on May 13, 2015, in the Korean Intellectual Property Office, the disclosure of each which is incorporated herein by reference in its entirety.

TECHNICAL FIELD

The present invention relates to a separation method for easily recovering normal butene from an olefin fraction including isobutene, isobutane, 1-butene, 2-butene, and normal butane, and a separation process system for separating normal butene.

BACKGROUND ART

The annual 1-butene demand growth rate has been 3% to 4%, and 1-butene is being used as a monomer for copolymerization of high density polyethylene (HDPE) or linear low density polyethylene (LLDPE). Recently, the price of 1-butene has been increased due to a supply and demand imbalance caused by an increase in the price of naphtha and a decrease in the utilization rate of naphtha cracking process due to high oil price.

A C4 residue generally obtained from the naphtha cracking process is composed of butadiene, isobutene, 1-butene, 2-butene, normal butane, and isobutane, and a fraction, in which butadiene is separated from the C4 residue, is referred to as "C4 residue I" (mixture of isobutene, 1-butene, 2-butene, butane, and isobutane). A fraction separated after isobutene is reacted with methanol to prepare methyl tertiary butyl ether (MTBE) is referred to as "C4 residue II" (mixture of 1-butene, 2-butene, butane, and isobutane). Also, a fraction, in which a trace of butadiene is removed by introducing the C4 residue II into a selective hydrogenation reactor, is referred to as "C4 residue 2.5".

In general, the production of 1-butene is performed in such a manner that a fraction remaining after separating isobutene from the C4 residue 2.5 is introduced into a distillation column to obtain 1-butene having a purity of 99% or more from the top of the column, and a C4 residue III, as a mixture of 1-butene, 2-butene, and normal butane, is obtained from the bottom of the column. The C4 residue III, with an overhead fraction of the isobutane distillation column, is prepared into liquefied petroleum gas (LPG) by a hydrogenation reaction. Also, the C4 residue III is separated into olefin and paraffin, and the olefin is concentrated to a concentration of 98 wt % of more and is then used to prepare methyl ethyl ketone (MEK) or prepare 1,3-butadiene by oxidative dehydrogenation. Furthermore, 1-butene and 2-butene are used to generate propylene through an exchange reaction or may be used to generate ethylene and hexane through an exchange reaction. In this case, in order to economically utilize the C4 residue II and the C4 residue III, 1-butene and 2-butene must be recovered from the resides (C4 residue II and C4 residue III) as much as possible, but since boiling points of the 1-butene and the 2-butene contained in the residues are very similar, it may not be possible to separate the 1-butene and the 2-butene by distillation unless using a lot of means. Thus, a significant amount of research related to a separation process of isobutene and 1-butene has been conducted, and a method of using isomerization of 1-butene and 2-butene has been introduced as a typical example.

Figure 1:
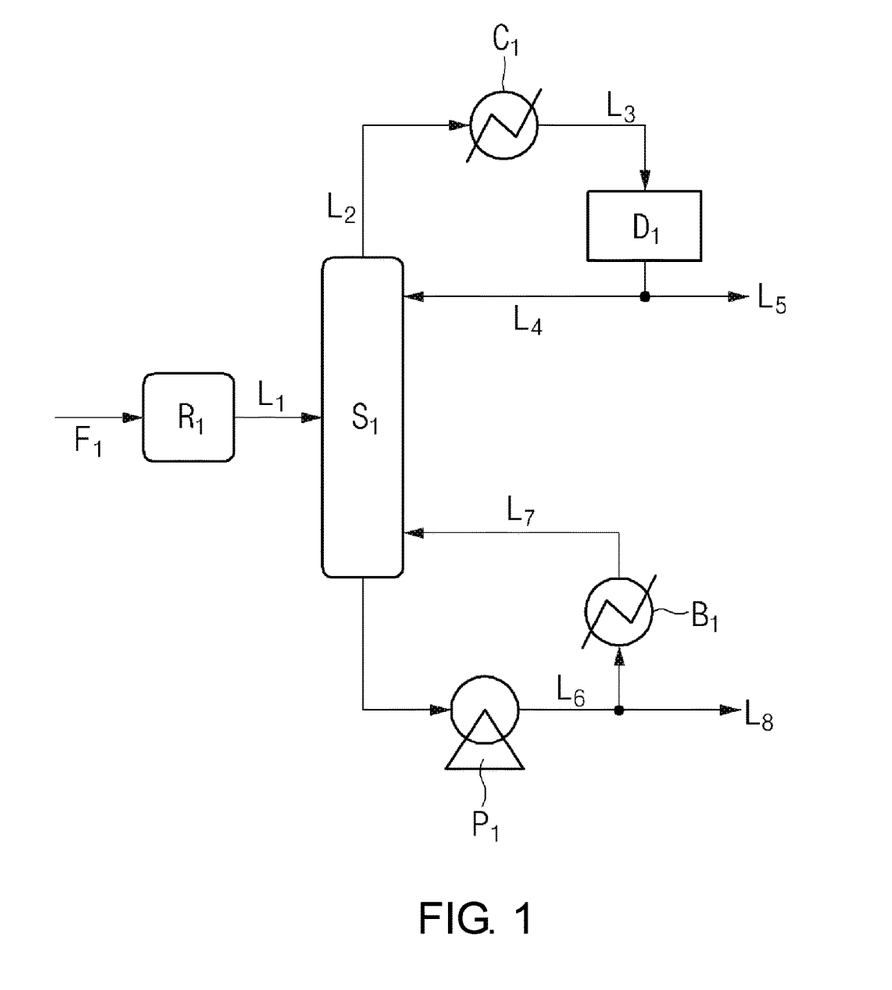
FIG. 1 schematically illustrates a conventional process system for separating normal butene from a typical olefin fraction.

Hereinafter, a conventional processing method will be described with reference to FIG. 1, wherein, as illustrated in FIG. 1, a conventional separation process has been performed by a process system including an isomerization reactor R1, a distillation column S1, a condenser C1, a reflux drum D1, a pump P1, and a reboiler B1. For example, an olefin fraction including isobutene, 1-butene, and 2-butene is supplied to the isomerization reactor R1 through a reactant supply line F1 and is then supplied to the distillation column S1 through a reaction product fraction transfer line L1 after a portion of the 1-butene is converted into 2-butene. The supplied reaction product is separated in the distillation column S1 so that a top fraction including isobutene is transferred to the condenser C1 through an overhead discharge line L2, condensed, and then introduced into the reflux drum D1 through reflux line 4 L3. A liquid in the top fraction in the reflux drum D1 is reintroduced into the distillation column S1 through reflux line 5 L4, and a gas is discharged through a recovery line L5. A bottom fraction including normal butene is transferred to a recovery line L8 through a bottom discharge line L6 and discharged, or is transferred to the reboiler B1, vaporized, and then reintroduced into the distillation column S1 through reflux line 6 L7. With respect to the conventional method as described above, since the isomerization reactor must not only be separately provided but also there is a need to use the condenser and reboiler, a process may be somewhat cumbersome and economic efficiency may not be good.

Thus, there is a need to develop a process which may easily recover normal butene from a reaction mixture including isobutene, isobutane, 1-butene, and 2-butene and may increase the economic efficiency while having high separation and recovery efficiency.

PRIOR ART DOCUMENT (Patent Document 1) JP2000-0029848 A

DISCLOSURE OF THE INVENTION

Technical Problem

An aspect of the present invention provides a separation method for easily recovering normal butene composed of 1-butene and 2-butene from an olefin fraction including isobutene, isobutane, 1-butene, 2-butene, and normal butane.

Another aspect of the present invention provides a separation process system for easily recovering normal butene from an olefin fraction.

Technical Solution

According to an aspect of the present invention, there is provided a separation method for recovering normal butene from an olefin fraction including the steps of: introducing an olefin fraction into a distillation column including at least one isomerization reaction zone (step 1); recovering a top fraction including isobutene and isobutane from a top of the distillation column and recovering a bottom fraction including normal butene from a bottom of the distillation column (step 2); compressing at least a portion of the top fraction to be heat-exchanged with at least a portion of the bottom fraction (step 3); and reintroducing at least a portion of the heat-exchanged top fraction and at least a portion of the bottom fraction into the top and the bottom of the distillation column, respectively (step 4).

According to another aspect of the present invention, there is provided a separation process system for recovering normal butene from an olefin fraction including: a supply unit which supplies a reactant including an olefin fraction; a processing unit connected to the supply unit, in which a distillation column including at least one isomerization reaction zone is disposed; and a recovery unit which is connected to the processing unit and recovers a reaction product, wherein the distillation column of the processing unit includes an overhead discharge line and a bottom discharge line, and the recovery unit includes a top fraction recovery unit connected to the overhead discharge line and a bottom fraction recovery unit connected to the bottom discharge line.

Advantageous Effects

Since a separation method for separating normal butene from an olefin fraction according to the present invention may easily convert 1-butene included in the olefin fraction to 2-butene, normal butene may be effectively separated and recovered by factional distillation and each recovered fraction may be easily refluxed even if the use of a reflux system using a refrigerant is reduced or excluded. Thus, economic efficiency may be improved and simultaneously, separation efficiency may be increased.

BRIEF DESCRIPTION OF THE DRAWINGS

The following drawings attached to the specification illustrate preferred examples of the present invention by example, and serve to enable technical concepts of the present invention to be further understood together with detailed description of the invention given below, and therefore the present invention should not be interpreted only with matters in such drawings.

MODE FOR CARRYING OUT THE INVENTION

Hereinafter, the present invention will be described in more detail to allow for a clearer understanding of the present invention.

It will be understood that words or terms used in the specification and claims shall not be interpreted as the meaning defined in commonly used dictionaries. It will be further understood that the words or terms should be interpreted as having a meaning that is consistent with their meaning in the context of the relevant art and the technical idea of the invention, based on the principle that an inventor may properly define the meaning of the words or terms to best explain the invention.

The present invention provides a separation method for recovering normal butene from an olefin fraction which may maximize a recovery rate of the normal butene while reducing economic costs.

In general, normal butene (1-butene and 2-butene) may be used in the preparation of propylene or may be used in the production of ethylene and hexene, and particularly, 1-butene is used as a monomer for copolymerization of high density polyethylene (HDPE) or linear low density polyethylene (LLDPE). The normal butene may be recovered from a C4 residue or the like obtained from a naphtha cracking process and used. However, since isobutene and isobutane, in addition to the normal butene (1-butene and 2-butene), are included in the C4 residue or the like and boiling points of the 1-butene (−6.24° C.) and the isobutene (−6.9° C.) are very similar, it is almost impossible to separate the 1-butene and the isobutene simply by fractional distillation, a complicated process may be required to separate the 1-butene and the isobutene, and economic efficiency may not be good. Thus, the 1-butene and the isobutene must be easily separated in order to increase economic utilization of the normal butene (1-butene and 2-butene). Thus, the present invention provides a separation method for easily recovering normal butene from an olefin fraction by converting 1-butene in the olefin fraction including isobutene, isobutane, 1-butene, and 2-butene to 2-butene using a distillation column, in which an isomerization reaction zone is included, and simultaneously performing fractional distillation.

The separation method according to an embodiment of the present invention includes the steps of: introducing an olefin fraction into a distillation column including at least one isomerization reaction zone (step 1); recovering a top fraction including isobutene and isobutane from a top of the distillation column and recovering a bottom fraction including normal butene from a bottom of the distillation column (step 2); compressing at least a portion of the top fraction to be heat-exchanged with at least a portion of the bottom fraction (step 3); and reintroducing at least a portion of the heat-exchanged top fraction and at least a portion of the bottom fraction into the top and the bottom of the distillation column, respectively (step 4).

Herein, the separation method for recovering normal butene may be a method of preparing normal butene, and, in this case, the normal butene may partially include 1-butene, but 2-butene may be a main component.

Step 1 is for facilitating the separation from isobutene by converting 1-butene included in an olefin fraction into 2-butene and performing fractional distillation, wherein it is a step of introducing the olefin fraction into a distillation column including an isomerization reaction zone.

The olefin fraction may include isobutene, isobutane, 1-butene, 2-butene, and normal butane. Specifically, the olefin fraction may be a C4 residue obtained from naphtha cracking and may be C4 residue I, in which butadiene is removed from the C4 residue, C4 residue II, C4 residue 2.5, C4 residue III, or a combination thereof. In this case, the olefin fraction may include less than 60 wt % of butadiene based on a total weight of the fraction, and an amount of the 1-butene in the olefin fraction may be in a range of 1 wt % to 500 wt % based on the 2-butene.

The isomerization reaction zone may be a region in which at least a portion of the 1-butene in the olefin fraction is converted to 2-butene. Specifically, the isomerization reaction zone may be a region in which selective positional isomerization occurs, and the selective positional isomerization may denote isomerization in which regioselective conversion of one isomer to another isomer occurs. That is, the isomerization reaction zone according to the present invention may be a region in which at least a portion of 1-butene is converted to 2-butene by the selective positional isomerization.

The expression "at least a portion" used in the present invention denotes a minimum of one or more portions, wherein at least a portion of 1-butene, for example, may represent a portion of the 1-butene, a portion or more of the 1-butene, or all of the 1-butene.

An isomerization catalyst may be included in the isomerization reaction zone according to an embodiment of the present invention, and the isomerization catalyst may be used without limitation as long as it is known in the art, but the isomerization catalyst, for example, may include at least one metal selected from the group consisting of ruthenium (Ru), rhodium (Rh), palladium (Pd), osmium (Os), iridium (Ir), platinum (Pt), nickel (Ni), tungsten (W), titanium (Ti), aluminum (Al), tantalum (Ta), niobium (Nb), molybdenum (Mo), vanadium (V), rhenium (Re), and gallium (Ga). The metal itself may be used as the catalyst, or the catalyst may be used in a state of being attached to a separate support. In a case in which the catalyst is used in a state of being attached to the support, the support may include at least one selected from the group consisting of silica-alumina, silica, zeolite, activated carbon, clay, alumina-based cement, rare earth metal oxide, and alkaline earth metal oxide.

A catalyst commercially available in the art may be purchased and used as the catalyst, or the catalyst may be prepared and used. Examples of the commercially available catalyst may be E-144 SDU (BASF) and E-445 SDU (BASF).

In a case in which the catalyst is prepared and used, a preparation method is not particularly limited, but the catalyst may be prepared by a method known in the art.

The distillation column according to an embodiment of the present invention includes an isomerization reaction zone in the inside thereof and has both isomerization reaction zone and distillation zone. That is, isomerization and fractional distillation may simultaneously occur in the same physical space, and the catalyst included in the isomerization reaction zone may not only be in contact with the olefin fraction introduced before the isomerization, but also may be in contact with at least a portion of the top fraction reintroduced into the top of the column and moving downward and may be in contact with at least a portion of the bottom fraction reintroduced into the bottom of the distillation column and moving upward. Thus, the isomerization reaction zone may be located at a midpoint of the distillation column for the smooth circulation of reactants (e.g., olefin fraction and reintroduced top fraction and bottom fraction) in the distillation column, and specifically, may be located at a position higher than the midpoint based on a total height of the distillation column. For example, the isomerization reaction zone may be located in the top 5% to 50% based on the total height of the distillation column.

Also, reaction conditions in the isomerization reaction zone may be related to fractional distillation conditions of the distillation zone. For example, pressures of the entire distillation column are set to the same level and a different temperature condition may be used for each zone. Specifically, the distillation zone of the top of the column may have a temperature of 0° C. to 190° C. under a pressure condition of 0.001 kgf/cm$^2$ to 20 kgf/cm$^2$, and the isomerization reaction zone may have a temperature of 5° C. to 200° C. under a pressure condition of 0.001 kgf/cm$^2$ to 20 kgf/cm$^2$.

In this case, when the temperature is less than 5° C., since the activity of the catalyst may be reduced, the isomerization in the isomerization reaction zone may not occur smoothly, and when the temperature is greater than 200° C., 1-butene may not be sufficiently converted due to an equilibrium.

The separation method according to the embodiment of the present invention may include introducing hydrogen into the distillation column, if necessary, before the performance of the isomerization in step 1. In this case, the separation method may further include separating hydrogen from the recovered top fraction, and the separated hydrogen may be reused.

Step 2 is a step for recovering a top fraction and a bottom fraction which are separated by the distillation column including the isomerization reaction zone.

The top fraction may include isobutene and isobutane, and may be recovered from the top of the distillation column. In this case, the top fraction may partially include unreacted 1-butene in addition to the isobutene and the isobutane, and an amount of the unreacted 1-butene included in the top fraction may be in a range of 0% to 10% based on a total flow (kg/hr) of the top fraction. The unreacted 1-butene may be reintroduced into the distillation column through steps 3 and 4 to be described later.

The bottom fraction may include normal butene and may be recovered from the bottom of the distillation column. The normal butene may partially include 1-butene, and 2-butene may be a main component. An amount of the 1-butene in the bottom fraction recovered from the bottom may be in a range of 0% to 5% based on a total flow (kg/hr) of the bottom fraction. In this case, the bottom fraction may partially include isobutene and isobutane in addition to the normal butene, and an amount of the isobutene and isobutane included in the bottom fraction may be in a range of 0% to 5% based on the total flow (kg/hr) of the bottom fraction.

Step 3 is a step of condensing at least a portion of the top fraction and vaporizing at least a portion of the bottom fraction in order to reintroduce at least a portion of each of the top fraction and the bottom fraction recovered in step 2 into the distillation column. Also, step is a step of respectively reintroducing the at least a portion of the condensed top fraction and the at least a portion of the vaporized bottom fraction in step 3 into the top and the bottom of the distillation column to allow them to again participate in the reaction.

As described above, the top fraction recovered from the top may partially include unreacted 1-butene, and the bottom fraction recovered from the bottom may partially include isobutene and isobutane. Thus, there is a need to reduce an amount of the consumed 1-butene by reintroducing the unreacted 1-butene included in the top fraction, and there is a need to increase purity of the normal butene in the bottom fraction by reducing an amount of the isobutene and isobutane in the bottom fraction through the reintroduction of the isobutene and isobutane included in the bottom fraction.

Conventionally, in order to achieve the above-described object, a method has been used in which a top fraction is reintroduced into a distillation column by condensing the top fraction recovered through a condenser using a refrigerant, and a bottom fraction is reintroduced into the distillation column by heating and vaporizing the bottom fraction recovered through a reboiler (see FIG. 1). However, a large amount of the refrigerant is necessary for the condensation, economic efficiency may be reduced due to the high price of the refrigerant, and a high cost is required in order for the reboiler to provide high heat.

In contrast, with respect to the method through step 3 according to the embodiment of the present invention, a process for achieving the above-described object may be performed without using separate condenser and reboiler, and thus, there is an effect of reducing economic costs.

Step 3 may be performed by compressing at least a portion of the recovered top fraction to be heat-exchanged with at least a portion of the bottom fraction. That is, the heat exchange according to an embodiment of the present invention may be performed by a difference between a temperature of the at least a portion of the top fraction and a temperature of the at least a portion of the bottom fraction, and the at least a portion of the top fraction and the at least a portion of the bottom fraction before the heat exchange may have a temperature difference of 5° C. to 200° C.

Specifically, the at least a portion of the top fraction before the heat exchange may have a temperature of 0° C. to 400° C. In this case, the at least a portion of the top fraction before the heat exchange may be subjected to a compression process in a compressor. Also, the at least a portion of the top fraction may be subjected to a step of proving heat to prevent condensation before the compression. In this case, the heat may be provided by a typical method known in the art, and, for example, a heat exchanger may be used.

Also, the at least a portion of the bottom fraction before the heat exchange may have a temperature of 5° C. to 200° C.

The at least a portion of the top fraction may be condensed by the heat exchange, and the at least a portion of the condensed top fraction may be reintroduced into the top of the distillation column as a reflux. In this case, a reintroduction rate (reflux ratio) of the at least a portion of the top fraction reintroduced into the top of the distillation column may be in a range of 50% to 99% based on the total flow (kg/hr) of the top fraction.

Furthermore, the at least a portion of the bottom fraction may be heated and vaporized by the heat exchange, and the at least a portion of the vaporized bottom fraction may be reintroduced into the bottom of the distillation column as a reflux. In this case, a reintroduction rate (reflux ratio) of the at least a portion of the bottom fraction reintroduced into the bottom of the distillation column may be in a range of 50% to 99% based on the total flow (kg/hr) of the bottom fraction.

Since the separation method according to the embodiment of the present invention may convert 1-butene to 2-butene by using the distillation column including the isomerization reaction zone and may simultaneously perform fractional distillation, isobutene and 1-butene may be easily separated without the use of a separate isomerization reactor, and at least a portion of the top fraction may be condensed and at least a portion of the bottom fraction may be vaporized through the heat exchange using the difference between the temperatures of the recovered top fraction and bottom fraction to be reintroduced into the distillation column. Thus, the process may be simplified and the economic efficiency may be improved.

1-butene and 2-butene may be separated by separate isomerization and fractional distillation of the recovered bottom fraction. In this case, the isomerization and fractional distillation may be performed by a typical method known in the art.

For example, the recovered bottom fraction is introduced into the distillation column including the isomerization reaction zone to convert a portion of 2-butene in the bottom fraction to 1-butene, and fraction distillation is performed to recover 1-butene from the top and recover 2-butene from the bottom so that the 1-butene and the 2-butene may be separated. In this case, the isomerization reaction zone may include a catalyst capable of regioselectively converting 2-butene to 1-butene.

Also, the present invention provides a separation process system for recovering normal butene from an olefin fraction. The separation process system may be used to perform a separation process by the above-described separation method.

The separation process system according to an embodiment of the present invention includes a supply unit which supplies a reactant including an olefin fraction; a processing unit connected to the supply unit, in which a distillation column including at least one isomerization reaction zone is disposed; and a recovery unit which is connected to the processing unit and recovers a reaction product, wherein the distillation column of the processing unit includes an overhead discharge line and a bottom discharge line, and the recovery unit includes a top fraction recovery unit connected to the overhead discharge line and a bottom fraction recovery unit connected to the bottom discharge line.

Hereinafter, the separation process system according to the embodiment of the present invention will be described with reference to FIG. 2. In this case, since descriptions other than equipment layout, design, and structure of the separation process system overlap with those described in the above-described separation method, the descriptions thereof will be omitted.

The supply unit is connected to the processing unit and may include a supply line 10 which supplies a reactant including an olefin fraction to the processing unit. The supply line may be connected to a stream in which a C4 residue is recovered from naphtha cracking. Also, the supply unit may further include a storage tank if necessary, and the storage tank may be disposed in the middle of the supply line and the stream, in which the C4 residue is recovered from the naphtha cracking, to control the flow of the reactant supplied to the processing unit. The reactant including an olefin fraction supplied through the supply line may include isobutene, isobutane, 1-butene, 2-butene, and normal butane. Specifically, the olefin fraction may be the same as described above. For example, the olefin fraction may be a C4 residue obtained from naphtha cracking, and may be C4 residue I in which butadiene is removed from the C4 residue, C4 residue II, C4 residue 2.5, C4 residue III, or a combination thereof.

Also, the supply unit may further include a hydrogen supply line which supplies hydrogen to the processing unit.

The processing unit may include a distillation column 30 including an isomerization reaction zone 31, and the distillation column 30 may be connected to the supply line 10 through which the reactant is supplied. The supply line 10 may be connected to a midpoint in a height direction of the distillation column 30 or may be connected to a point at which the isomerization reaction zone 31 is included.

The isomerization reaction zone 31 may be a region in which selective isomerization, which converts at least a portion of 1-butene in the reactant introduced through the supply line 10 to 2-butene, is performed, and an isomerization catalyst may be included in the isomerization reaction zone 31. In this case, the isomerization catalyst may be the same as described above.

The isomerization reaction zone is not particularly limited, but the isomerization reaction zone may be located in the top 5% to 50% of the total height of the distillation column for smooth isomerization. That is, the isomerization reaction zone 31 may be disposed at a position higher than the midpoint in the height direction of the distillation column 30.

Furthermore, the distillation column 30 of the processing unit may include an overhead discharge line 11 for discharging a top fraction separated by fractional distillation and a bottom discharge line 20 for discharging a bottom fraction.

The recovery unit is connected to the processing unit to recover a reaction product separated through the distillation column 30 of the processing unit, wherein the recovery unit may include a top fraction recovery unit connected to the overhead discharge line 11 and a bottom fraction recovery unit connected to the bottom discharge line 20, and the top fraction recovery unit and the bottom fraction recovery unit may respectively include a first reflux line and a second reflux line which are configured to reintroduce at least a portion of each fraction into the processing unit. Herein, the first reflux line, as a transfer line for refluxing the top fraction, may include reflux line-1 12, reflux line-2 13, reflux line-4 14, and reflux line-5 18 which will be described later, and the second reflux line, as a transfer line for refluxing the bottom fraction, may include reflux line-3 21 and reflux line-6 22 which will be described later.

Specifically, a compressor 33, a heat exchanger 36, and a reflux drum 34 may be disposed in the recovery unit, and the recovery unit may be connected to the compressor 33, the heat exchanger 36, and the reflux drum 34 to include a plurality of lines that transfer the top fraction or the bottom fraction.

The top fraction recovery unit may include a top fraction recovery line 19, which recovers the top fraction transferred from the overhead discharge line 11, and the plurality of reflux lines for reintroducing at least a portion of the fraction into the processing unit. The overhead discharge line 11 may be connected to the reflux drum 34 of the top fraction recovery unit, and the top fraction may be transferred into the reflux drum 34 through the overhead discharge line 11. Also, the at least a portion of the top fraction may be transferred to the compressor 33 through the reflux line-1 12 which is connected to the overhead discharge line 11. In this case, the top fraction transferred through the overhead discharge line 11 may be heated by the heat exchanger and may then be transferred to the reflux drum 34 or the compressor 33. Furthermore, the reflux drum 34 may be connected to the reflux line-4 14, and at least a portion of the top fraction condensed through the reflux line-4 14 may be transferred to the reflux drum 34. The at least a portion of the top fraction transferred to the compressor 33 may be compressed and transferred to the heat exchanger 36 through the reflux line-2 13 which is connected to the heat exchanger 36.

Also, the bottom fraction recovery unit may include a bottom fraction recovery line 23, which recovers the bottom fraction transferred from the bottom discharge line 20, and the plurality of reflux lines for reintroducing at least a portion of the bottom fraction into the processing unit. The bottom fraction may be discharged to the bottom fraction recovery line 23 through the bottom discharge line 20 and recovered, and the at least a portion of the bottom fraction may be transferred to the heat exchanger through the reflux line 3 21 which is connected to the heat exchanger 36.

The heat exchanger 36 may be operated by the heat exchange between the at least a portion of the top fraction transferred through the reflux line-2 13 and the at least a portion of the bottom fraction transferred through the reflux line-3 21, and thus, the at least a portion of the top fraction may be condensed and the at least a portion of the bottom fraction may be vaporized.

The at least a portion of the condensed top fraction may be transferred to the reflux drum 34 through the reflux line-4 14 as described above. The gas-phase top fraction transferred from the overhead discharge line 11 and at least a portion of the liquid-phase top fraction transferred through the reflux line-4 14 are included in the reflux drum 34, and the liquid phase and gas phase are separated through the reflux drum 34 so that the at least a portion of the liquid-phase top fraction is reintroduced into the processing unit through the reflux line-5 18, and the gas-phase top fraction may be discharged through the top fraction recovery line 19 and recovered.

Also, at least a portion of the vaporized bottom fraction may be reintroduced into the processing unit through the reflux line-6 22.

As described above, since the separation process system according to the embodiment of the present invention isomerizes 1-butene into 2-butene through the processing unit in which the distillation column including the isomerization reaction zone is disposed, 1-butene and isobutene may not only be easily separated, but each fraction may also be effectively refluxed into the processing unit without the use of a separate reflux system (e.g., condenser and reboiler). Thus, process efficiency may be improved and simultaneously, economic costs may be reduced.

Hereinafter, the present invention will be described in more detail, according to the following examples. However, the following examples are merely presented to exemplify the present invention, and the scope of the present invention is not limited thereto.

In the following example and comparative example, the separation method according to the present invention was simulated by using ASPEN PLUS, a commercial process simulation program. Program's built-in values, values described in the literature, and values obtained from conventional C4 separation and manufacturing processes were used as constants required for the simulation.

Example

In a distillation column including an isomerization reaction zone, a number of theoretical plates was set to 100, the isomerization reaction zone was set between the 20th plate and the 40th plate, a top pressure was fixed to 4 kgf/cm$^2$G, a temperature of the top of the distillation column was adjusted to 39° C., and a temperature of the isomerization reaction zone was adjusted to be in a range of 46° C. to 51° C. A selectivity of a catalyst included in the isomerization reaction zone was assumed to be 100%. An olefin fraction, as a reactant, was set to have a composition including 0.5 wt % of propylene, 25.0 wt % of isobutane, 20.0 wt % of isobutene, 15.0 wt % of 1-butene, 31.0 wt % of 2-butene, 8.0 wt % of normal butane, and 0.5 wt % of normal pentane, and a total flow was set to 10,000 kg/hr. Reflux ratios of refluxed top fraction and bottom fraction were respectively adjusted to be 96.37% and 95.76%, and results of process performance are presented in the following Table 1. In this case, heat duty was 0 Gcal/hr and cooling duty was −1.14 Gcal/hr.

TABLE 1

| Category | Reactant (wt %) | Recovered top fraction (wt %) | Recovered bottom fraction (wt %) |
|---|---|---|---|
| Propylene | 0.5 | 1.09 | 0.0 |
| Isobutane | 25.0 | 54.32 | 0.0 |
| Isobutene | 20.0 | 43.27 | 0.16 |

TABLE 1-continued

| Category | Reactant (wt %) | Recovered top fraction (wt %) | Recovered bottom fraction (wt %) |
|---|---|---|---|
| 1-butene | 15.0 | 0.3 | 0.08 |
| Normal butane | 8.0 | 0.83 | 14.11 |
| 2-butene | 31.0 | 0.19 | 84.73 |
| Normal pentane | 0.5 | 0.0 | 0.93 |
| Total flow (kg/hr) | 10,000 | 4.602 | 5.398 |

Comparative Example

Figure 2:
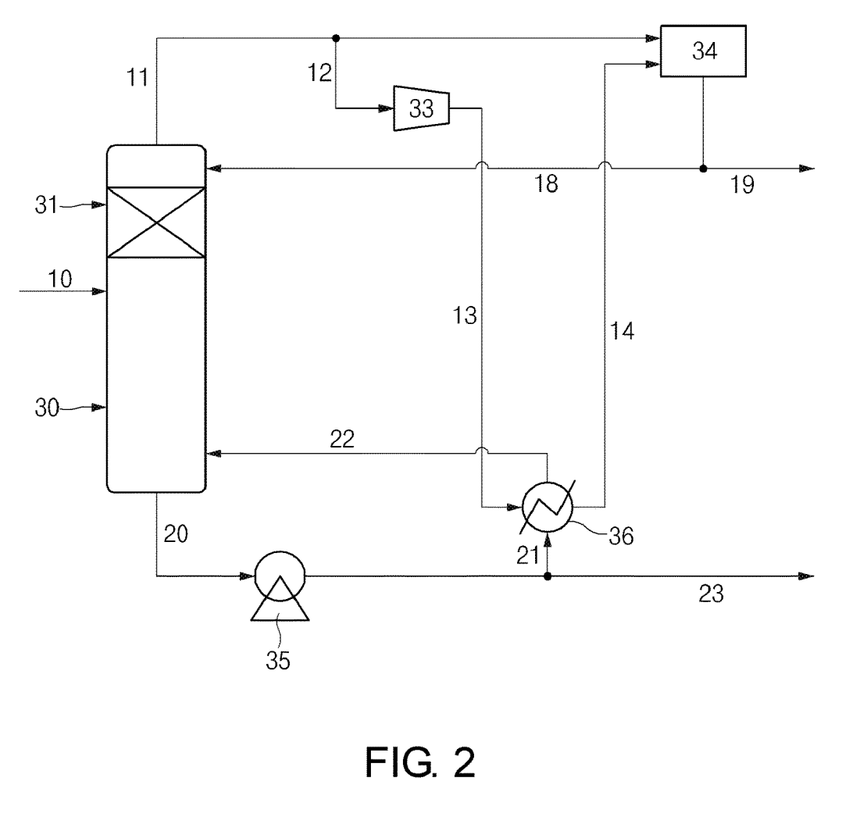
FIG. 2 schematically illustrates a separation process system for separating normal butene from an olefin fraction according to an embodiment of the present invention.

A process was performed by using the same conditions as those of the example except that a simulation was performed by a process system as illustrated in FIG. 2 and conditions of an isomerization reactor was separately set. In this case, the isomerization reactor was set to a temperature of 50° C. and a pressure of 4.8 kgf/cm²G. Results were presented in the following Table 2, heat duty was 10.06 Gcal/hr, and cooling duty was −10.01 Gcal/hr.

TABLE 2

| Category | Reactant (wt %) | Fraction discharged from reactor (wt %) | Recovered top fraction (wt %) | Recovered bottom fraction (wt %) |
|---|---|---|---|---|
| Propylene | 0.5 | 0.5 | 1.09 | 0.0 |
| Isobutane | 25.0 | 25.0 | 54.34 | 0.01 |
| Isobutene | 20.0 | 20.0 | 40.84 | 2.25 |
| 1-butene | 15.0 | 1.8 | 3.74 | 0.14 |
| Normal butane | 8.0 | 8.0 | 0.0 | 14.81 |
| 2-butene | 31.0 | 44.20 | 0.0 | 81.83 |
| Normal pentane | 0.5 | 0.5 | 0.0 | 0.93 |
| Total flow (kg/hr) | 10,000 | 10,000 | 4,600 | 5,400 |

As illustrated in Tables 1 and 2, with respect to the separation process of the example according to an embodiment of the present invention, a composition ratio of unreacted 1-butene in the recovered top fraction was 0.3 wt %, but, with respect to the separation process of the comparative example, a composition ratio of unreacted 1-butene in the recovered top fraction was 3.74 wt %. Also, with respect to the separation process according to the example, a composition ratio of isobutene in the recovered bottom fraction was 0.16 wt %, but, with respect to the separation process of the comparative example, a composition ratio of isobutene in the recovered bottom fraction was 2.25 wt %. That is, the amount of the unreacted 1-butene in the top fraction separated by the separation process according to the example was decreased by about 1/12 in comparison to the separation process of the comparative example, and the amount of the isobutene in the bottom fraction was decreased by about 1/13 in comparison to the separation process of the comparative example.

Furthermore, with respect to the separation process of the example according to the embodiment of the present invention, since the top fraction was condensed and refluxed and the bottom fraction was vaporized and refluxed by the heat exchange between the two fractions using a temperature difference between the top fraction and the bottom fraction without the use of a separate reflux system (condenser and reboiler) for refluxing each of the top fraction and the bottom fraction, heat duty was reduced by 100% and cooling duty was reduced by about 88% in comparison to the separation process of the comparative example using a separate reflux system.

As confirmed by the above results, with respect to the separation process of the example according to the embodiment of the present invention, since 1-butene was converted to 2-butene by using the distillation column including the isomerization reaction zone and simultaneously, fractional distillation was performed, isobutene and 1-butene may be easily separated by a simplified process. In addition, since a separate reflux system was not used, an effect of reducing costs may be obtained. Also, as can be seen from the composition ratios of the top fraction and the bottom fraction, the separation process according to the embodiment of the present invention may easily reflux each of the top fraction and the bottom fraction without the use of a separate reflux system.

Thus, since the separation method and separation process system for recovering normal butene from an olefin fraction according to the present invention may effectively separate isobutene and 1-butene from the olefin fraction including isobutene, isobutane, 1-butene, and 2-butene by a simplified process, high-purity normal butene may be recovered. Simultaneously, since each of the recovered top fraction and bottom fraction may be refluxed without the separate use of condenser and reboiler, separation efficiency may be further increased while reducing costs.

The invention claimed is:

1. A separation system for recovering normal butene from an olefin fraction, the separation system comprising:
   a supply unit that supplies a reactant including an olefin fraction;
   a processing unit connected to the supply unit, in which a single distillation column is disposed, the distillation column including:
      at least one isomerization reaction zone;
      at least one distillation zone;
      an overhead discharge line; and
      a bottom discharge line; and
   a recovery unit that is connected to the processing unit and recovers a reaction product, the recovery unit comprising a heat exchanger, a top fraction recovery unit connected to the overhead discharge line of the distillation column to recover a top fraction, and a bottom fraction recovery unit connected to the bottom discharge line of the distillation column to recover a bottom fraction, the heat exchanger refluxing each of the top fraction and the bottom fraction without the use of a separate reflux system comprising a condenser and reboiler.

2. The separation system of claim 1, wherein the supply unit comprises a supply line which transfers the reactant to the processing unit, and
   the supply line is connected to a stream in which a C4 residue is recovered from naphtha cracking.

3. The separation system of claim 1, wherein the supply unit further comprises a hydrogen supply line that supplies hydrogen to the processing unit.

4. The separation system of claim 1, wherein the isomerization reaction zone is located in top 5% to 50% of a total height of the distillation column.

5. The separation system of claim 1, wherein the top fraction recovery unit comprises a first reflux line that reintroduces at least a portion of the top fraction into the processing unit, and
   the bottom fraction recovery unit comprises a second reflux line that reintroduces at least a portion of the bottom fraction into the processing unit.

6. The separation system of claim 5, wherein:
the recovery unit further comprises a compressor and a reflux drum;
the first reflux line is sequentially connected to the compressor, the heat exchanger, the reflux drum, and the processing unit, and
the second reflux line is sequentially connected to the heat exchanger and the processing unit.

7. The separation system of claim 6, wherein:
the compressor compresses at least a portion of the top fraction to yield a compressed top fraction; and
the heat exchanger performs heat exchange between at least a portion of the compressed top fraction transferred through the first reflux line and at least a portion of the bottom fraction transferred through the second reflux line, refluxing each of the top fraction and the bottom fraction without the use of a separate reflux system comprising a condenser and reboiler.

* * * * *